United States Patent [19]

Hawkins

[11] Patent Number: 5,583,258
[45] Date of Patent: Dec. 10, 1996

[54] PROCESS FOR PREPARING MONO-LONG CHAIN AMINE OXIDE SURFACTANTS

[75] Inventor: Gene P. Hawkins, Oregonia, Ohio

[73] Assignee: The Procter & Gamble Company, Cincinnati, Ohio

[21] Appl. No.: 388,780

[22] Filed: Feb. 15, 1995

[51] Int. Cl.⁶ ................................................. C07C 291/04
[52] U.S. Cl. ................................................. 564/298
[58] Field of Search ............................................. 564/298

[56] References Cited

U.S. PATENT DOCUMENTS

| | | | |
|---|---|---|---|
| 3,333,000 | 7/1967 | Albert et al. ............................ | 260/583 |
| 4,960,934 | 10/1990 | Smith et al. ............................ | 564/298 |
| 5,223,644 | 6/1993 | Blezard et al. ............................ | 564/2 |
| 5,498,791 | 3/1996 | Blezard et al. ............................ | 564/2 |

*Primary Examiner*—Brian M. Burn
*Attorney, Agent, or Firm*—Thomas G. Krivulka

[57] ABSTRACT

Mono-long chain amine oxide surfactants can be prepared containing active levels of greater than about 30%, by weight of amine, and with low nitrite and nitrosamine levels when oxidized in the presence of bicarbonate material present at levels less than about 2.5%, by weight of amine, and without the presence of phase-modifying solvents.

13 Claims, No Drawings

PROCESS FOR PREPARING MONO-LONG CHAIN AMINE OXIDE SURFACTANTS

FIELD OF THE INVENTION

The present invention relates to an improvement in a chemical process for preparing mono-long chain amine oxide surfactants, whereby the active content of the surfactant is greater than about 30%, by weight of the amine, and nitrite and nitrosamine levels are suppressed.

BACKGROUND OF THE INVENTION

The preparation of mono-long chain amine oxide surfactants by the oxidation of tertiary amines is of considerable commercial interest. Such surfactants are widely used in commercial cleaning compositions, especially high sudsing dishwashing detergents. Such concentrated solutions are especially useful in formulating concentrated or "compact" liquid detergent compositions which are now favored by many consumers and generally contain lower amounts of water than conventional detergents. However, the formulation of mono-long chain amine oxide surfactants containing high levels, i.e., greater than about 30%, by weight of the amine, has proven to be a difficult problem to overcome. Typically, mono-long chain amine oxide surfactants containing above 30% active result in an unhandleable gel especially when a phase modifying solvent is not incorporated. It has also been discovered that some sources of mono-long chain amine oxide surfactants may be contaminated with residual amounts of nitrite materials, especially inorganic nitrites. Contamination by such nitrites may be tolerable under many circumstances. For some uses however, the presence of nitrites may be undesirable, since they can react with other ingredients which may be present in the fully formulated detergent compositions.

Detergent formulators presumably could arrange for special care to be taken during the manufacture of mono-long chain amine oxides in order to minimize the formation of undesirable nitrite contaminants. However, the manufacturer of high volume, low cost chemicals such as home-use detergents can ill afford surfactants and other raw materials requiring special reaction techniques or special reactants, due to their expense.

The present invention solves the viscosity problems and eliminates the concern about high nitrite/nitrosamine levels normally associated with mono-long chain amine oxide surfactants containing high active levels, i.e., greater than about 30%, by weight of the amine, using simple cost-effective techniques and without the use of phase modifying solvents. The invention herein thus affords access to a concentrated, high quality supply of this class of surfactants.

SUMMARY OF THE INVENTION

The present invention relates to a process for preparing mono-long chain amine oxide surfactants, which comprises:

A. dissolving less than about 2.5%, by weight of amine, of bicarbonate in water;

B. adding a tertiary amine having the general formula:

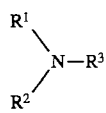

wherein each $R^1$ and $R^2$ are $C_1$-$C_4$ alkyl or hydroxyalkyl groups; and $R^3$ is a $C_8$ to $C_{18}$ alkyl or alkenyl group; and C. oxidizing said amine to form the corresponding mono-long chain amine oxide having the general formula:

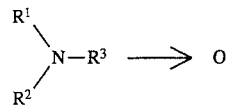

wherein $R^1$, $R^2$, and $R^3$ are defined as above; and whereby said mono-long chain amine oxide has a nitrite content below about 3 ppm, a nitrosamine content below about 500 ppb, and active level of greater than about 30%, by weight of amine, and wherein said process is essentially free of any phase-modifying solvent.

DETAILED DESCRIPTION OF THE INVENTION

The present invention relates to a process for preparing mono-long chain amine oxide surfactants, which comprises:

A. dissolving less than about 2.5%, by weight of amine, of bicarbonate in water;

B. adding a tertiary amine having the general formula:

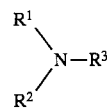

wherein each $R^1$ and $R^2$ are $C_1$-$C_4$ alkyl or hydroxyalkyl groups; and $R^3$ is a $C_8$ to $C_{18}$ alkyl or alkenyl group; and C. oxidizing said amine to form the corresponding mono-long chain amine oxide having the general formula:

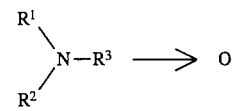

wherein $R^1$, $R^2$, and $R^3$ are defined as above; and whereby said mono-long chain amine oxide has a nitrite content below about 3 ppm, a nitrosamine content below about 500 ppb, and active level of greater than about 30%, by weight of amine, and wherein said process is essentially free of any phase-modifying solvent.

For purposes of clarity, the following defines the terms used herein.

By "nitrite" herein is meant the $NO_2^-$ species, including all forms of nitrous acid or its salts or reactive derivatives such as $HNO_2$, $NaNO_2$, $N_2O_3$, $H_2NO_2^+$, $N_2O_4$, $NO^{+\cdot}$ or related species.

Amine

The present invention encompasses an improved process for preparing mono-long chain amine oxide surfactants having the general formula:

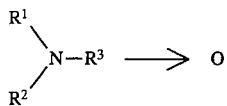

wherein each $R^1$ and $R^2$ are $C_1$-$C_4$ alkyl or hydroxyalkyl groups, preferably methyl groups, and $R^3$ is a $C_8$ to $C_{18}$, preferably a $C_{10}$-$C_{18}$, more preferably a $C_{12}$-$C_{16}$ alkyl or alkenyl group. The improvement consists of the oxidation of the corresponding amine of the formula $R^1 R^2 R^3 N$ in the presence of low levels, i.e., less than 2.5%, by weight of the amine, of bicarbonate material, whereby the mono-long chain amine oxide surfactant contains an active level of greater than about 30%, by weight of the amine, preferably from about 31% to about 38%, by weight of the amine, more preferably from about 32% to about 37%, by weight of the amine.

Bicarbonate Material

The bicarbonate material is selected from the group consisting of alkali metal bicarbonates, alkaline-earth bicarbonates, ammonium bicarbonates, and mixtures thereof. It will also be understood that bicarbonate precursors can be used in place of bicarbonate salts, e.g., alkali metal carbanates can be used to generate bicarbonate in situ. Typically, said bicarbonate material is sodium carbonate used to generate bicarbonate in situ, preferably said bicarbonate material is ammonium bicarbonate, and more preferably, sodium bicarbonate. The bicarbonate material is preferably present at a level less than about 2.5%, by weight of amine, more preferably at a level of from about 0.3% to about 2.0%, by weight of amine, and most preferably at a level of from about 0.5% to about 1.5%, by weight of amine.

Process

The oxidation step herein is preferably conducted using hydrogen peroxide or source of hydrogen peroxide, or by hydrogen peroxide generated in situ.

When conducted in the presence of bicarbonate material, the process is preferably carried out at a pH in the range of from about 6 to about 10, preferably from about 7 to about 10 more preferably from about 8 to about 10.

Typically, amine oxide surfactants are produced by oxidizing the desired amine with hydrogen peroxide, which is generally in the form of a 5% to 70% aqueous solution. Although less can be used, typically the hydrogen peroxide is used at about a 5% to 10% excess of the stoichoimetric amount when conversion of more than 99% of the tertiary amine is required. It is preferable in the present invention to use peroxide levels of from about 95% to about 125% of the stoichiometric amount, more preferably from about 100% to about 115%, of the stoichiometric amount, and to conduct the process at a temperature of from about 40° C. to about 100° C., preferably from about 50° C. to about 85° C., and more preferably from about 50° C. to about 75° C. When hydrogen peroxide is used as the oxidizing agent in the present invention it is typically used at a level of from about 13% to about 20%, by weight of amine, preferably from about 14% to about 18%, and more preferably from about 15% to about 17%, by weight of amine. Total reaction time is typically 2 to 20 hours depending on reaction stoichiometry, catalyst, solvent system and degree of tertiary amine conversion required. Commercially, either batch or continuous reaction processes are used. If desired, peroxide reaction residues can be reduced or eliminated by adding a reducing agent, such as sodium sulfite, or other agent to promote peroxide decomposition. However, such peroxide residues can be beneficial for the reduction of nitrite levels under acidic conditions.

Some mono-long chain amine oxide surfactants prepared in the foregoing, standard manner with active levels of greater than about 30%, by weight of amine, have now been found to be contaminated with as much as 60 ppm of nitrite and found to produce an unhandleable gel. The use of bicarbonate material, such as sodium bicarbonate, reduces the nitrite levels in mono-long chain amine oxide to acceptable levels, under 3 ppm, preferably under 1 ppm, more preferably under 0.05 ppm. The use of bicarbonate material also decreases nitrosamine levels to less than detection limits of 500 ppb, preferably less than 250 ppb, more preferably less than 100 ppb, as measured by standard nitrite analyses, while still allowing high active levels. The present process lowers these nitrite and nitrosamine levels while increasing the active level to more than about 30%, by weight of amine.

In the process of this invention the oxidation of the amine is carried out using otherwise conventional procedures, as noted above, but with the addition of bicarbonate materials at levels less than about 2.5%, by weight of amine.

Nitrite Analyses

The presence of nitrites in the mono-long chain amine oxide surfactants, both before and after use of the procedures of this invention, can be measured in several ways. The following are illustrative.

a) Nitrite test strips, sold under the trademark E. M. Quant, Catalog number 10007-1 (Division of EM Industries, Inc., Gibbstown, N.J.) are used in standard fashion as directed by the manufacturer. These test strips are convenient and quite suitable under most conditions.

b) If more precise measurement is needed, nitrite can be assayed spectrophotometrically (Varian Spectrophotometer Model 219) using a colorimetric assay with sulfanilamide reagent (5 g. sulfanilamide, 60 ml conc. HCl diluted to 500 ml in $H_2O$) and N-(1-naphthyl)-ethyleneodiamine dihydrochloride "NED" (500 mg diluted to 500 ml in $H_2O$; stored in a dark bottle and replaced if the solution develops a strong brown color). The test employs a 5 ml test solution of the amine oxide surfactant at 3–30% concentrations, depending on nitrite concentration. In the test, 0.1 ml of the sulfanilamide reagent is added to the amine oxide solution. After 5 minutes, the pH is adjusted to 1.0–1.5 using HCl. Then, 0.1 ml of the NED solution is added. Color develops fully within a few hours. The absorbance is measured at 543 nanometer (nm) wavelength. The results are compared with samples to which known amounts of nitrite have been intentionally added.

(c) In cases where a large excess of nitrite scavenger is present, nitrite concentration can be determined by chromatographic separation methods, either by ion exchange chromatography or capillary zone electrophoresis. The invention thus provides stable detergent compositions (especially liquid compositions) comprising mono-long chain amine oxide detergent surfactants prepared in the foregoing manner.

All percentages, ratios and proportions herein are by weight, unless otherwise specified. All documents cited are incorporated here by reference.

EXAMPLES I–III

| INGREDIENT | I Wt. % | II Wt. % | III Wt. % | IV Wt. % |
|---|---|---|---|---|
| Amine[1] | 32 | 34 | 35 | 35 |
| 50% $H_2O_2$ | 10 | 11 | 11 | 11 |
| $NaHCO_3$ | 2 | 2 | 0.7 | — |
| Water | 56 | 53 | 53.3 | 54 |

[1]$C_{12-16}$ Alkyl Dimethylamine

Preparation of Examples I–IV $NaHCO_3$ is dissolved into the water and the amine is added with agitation. $H_2O_2$, when present, is added while temperature is about 25° C. Temperature is raised to about 68° C. and cooling is applied to hold temperature to between about 60° C. and 68° C. The surfactant prepared by this technique is an easily handleable aqueous solution of a mono-long chain amine oxide containing active levels of greater than about 30%, by weight of amine. The material prepared by this process exhibits nitrite and nitrosamine levels significantly lower than are seen in the absence of bicarbonate. Example IV, which is prepared without the use of bicarbonate results in an unhandleable gel.

DETERGENT FORMULATIONS

Surfactants and Suds Enhancers—The substantially nitrite-free, concentrated, mono-long chain amine oxide surfactants afforded by the present invention are useful in any circumstance where the prospective reaction of nitrite with the detersive ingredients is desirably avoided and high active levels are desirable. The amine oxides herein are especially preferred for use in liquid detergents.

The following is intended to illustrate the use of the amine oxide surfactants made in accordance with this invention in liquid detergent compositions, but is not intended to be limiting thereof. Water-soluble $Ca^{++}$ or $Mg^{++}$ salts, e.g., $MgSO_4$, $MgCl_2$ or the like can be used to introduce such cations into the compositions, typically at levels of 0.01% –2%, to enhance sudsing and grease removal performance.

EXAMPLE V

Homogeneous light duty liquid detergent compositions which are especially adapted for dishwashing and other hard surface cleaning operations are as follows. In the Examples A–D, the surfactants comprise various alkyl ethoxy sulfate surfactants which, using standard terminology, are abbreviated to indicate their average degree of ethoxylation; thus $C_{12-13}$ EO(0.8) sulfate indicates a sulfated mixed ethoxylated $C_{12}$-$C_{13}$ alcohol fraction having an average degree of ethoxylation of about 0.8. These anionic ethoxy sulfates are preferably used in their $Na^+$ or $NH_4^+$ salt form. The $C_{12}$-$C_{16}$ mono-long chain amine oxide is a mixed $C_{12-14-16}$ (average) dimethyl amine oxide. The mono-long chain amine oxide is prepared in the manner of Examples I, II and III, herein, respectively, for use in compositions A, B, C and D, respectively. The $C_{12-14}$ AP betaine is $C_{12}/_{14}H_{25}/_{29}CONH(CH_2)_3N^+(CH_3)_2$-$CH_2CO_2^-$. The $C_{12-14}$ AP sultaine is $C_{12}/C_{14}H_{25}/_{29}CONH(CH_2)_3N+(CH_3)_2CH_2CH(OH)CH_2SO_3^-$. The $C_{12-14}$ DM betaine is $C_{12}/_{14}H_{25}/_{29}N+ (CH_3)_2CH_2CO_2^-$. The ethoxylated nonionic surfactant designated $C_{9-11}EO(8)$ refers to $C_9$-$C_{11}$ alcohols ethoxylated with an average of 8 moles of ethylene oxide. The $Ca^{++}$ and $Mg^{++}$ cations are conveniently introduced into the compositions as $CaCl_2$ and $MgCl_2$. The balance of the compositions comprises water and citrate/propylene glycol present in the glucamide surfactant (1–5%) and 1–3% cumene sulfonate or xylene sulfonate hydrotope. The pH is typically 6.8–7.4 ($NH4^+$ salts) or 7–8.2 ($Na^+$ salts).

| Ingredient* | A Wt. % | B Wt. % | C Wt. % | D Wt. % |
|---|---|---|---|---|
| $C_{12-14}$ N-methyl glucamide** | 11 | 8 | 12.7 | 9 |
| $C_{12-13}$ EO(0.8) sulfate | — | 13 | 10.0 | 9 |
| $C_{12-14}$ EO(3) sulfate | 11 | — | 2.7 | 14 |
| $C_{12-13}$ EO(6.5) sulfate | — | — | — | 3 |
| $C_{12-14}$ AP betaine | — | — | 2 | — |
| $C_{12-14}$ AP sultaine | — | — | — | 1.0 |
| $C_{12-13}$ dimethyl amine oxide[2] | 2.5 | 3.0 | 2.5 | 1.0 |
| $C_{12-14}$ DM betaine | — | 2.0 | — | — |
| $C_{9-1}$ EO(8) | 0.5 | 8 | 7 | — |
| $Ca^{++}$ | — | — | 0.5 | 1.0 |
| $Mg^{++}$ | 0.9 | 0.25 | — | — |
| Balance | bal | bal | bal | bal |

*Commercial grade surfactants may be bleached to colorless (i.e., to provide water-clear liquids). The $C_{12-14}$ N-methylglucamide herein preferably has been treated with acetic anhydride in water at 60° C.–80° C. so that it contains 0.1% or less of N-methylglucamine. Optionally, for highest sudsing the glucamide surfactant can also be treated with ethanolamine at 50° C.–80° C. to reduce levels of free fatty acids to 1% or below.
**Pretreated with acetic anhydride to decrease amine content.
[2]Substantially nitrite free, prepared according to this invention.

EXAMPLE IV

A liquid detergent composition with a suds boosting fatty amide is as follows. Product pH is adjusted to 7.8 with NaOH.

| Ingredient | % (wt.) |
|---|---|
| Dimethyldodecyl amine oxide[3] | 5.0 |
| $C_{12-14}$ EO(3) sulfate | 14.0 |
| Sodium cumene sulfonate[4] | 2.0 |
| $C_{12}$ Monoethanolamide | 1.5 |
| Coconut N-methylglucamide | 7.0 |
| Water, dye, minors | Balance |

[3]Substantially nitrite free, prepared according to this invention.
[4]Introduced in acid treatment of amine oxide as sulfonic acid form and subsequently neutralized with NaOH.

EXAMPLE VII

A 32–37% (wt.) "high active" solution of $C_{12-14}$ dimethyl amine oxide is prepared by oxidizing the corresponding amine with peroxide, with the following results.

| Run | Nitrite (ppm) |
|---|---|
| A. High active, no additives | 7.0 |
| B. High active, 0.8% $NaHCO_3$ | 0.5 |

While the foregoing illustrates the present invention and its use in liquid detergents, especially dishwashing compositions, it is not intended to limit the scope of the invention. The amine oxide surfactants provided by this invention can be used in any detergent composition where high sudsing, good grease/oil removal and overall product stability are desired. The invention herein can be used with various conventional ingredients to provide fully-formulated fabric laundering compositions, hard-surface cleansers, personal cleaning products and the like. Such compositions can be in the form of liquids, granules, bars and the like.

What is claimed is:

1. A process for preparing mono-long chain amine oxide surfactants, which comprises:

A. dissolving less than about 2.5%, by weight of amine, of bicarbonate, selected from the group consisting of alkali metal bicarbonates, alkaline-earth bicarbonates, bicarbonate precursors, and mixtures thereof, in water;

B. adding a tertiary amine having the general formula:

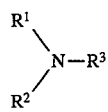

wherein each $R^1$ and $R^2$ are $C_1$-$C_4$ alkyl or hydroxyalkyl groups; and $R^3$ is a $C_8$ to $C_{18}$ alkyl or alkenyl group; and C. oxidizing said amine to form the corresponding mono-long chain amine oxide surfactant having the general formula:

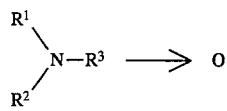

wherein $R^1$, $R^2$, and $R^3$ are defined as above; and whereby said mono-long chain amine oxide has a nitrite content below about 3 ppm, a nitrosamine content below about 500 ppb, and active content of said surfactant of greater than about 30%, by weight of the composition, and wherein said process is essentially free of any phase-modifying solvent.

2. The process according to claim 1 wherein the amine is a $C_{10}$-$C_{18}$ alkyl dimethylamine.

3. The process according claim 2 wherein said amine is a $C_{12}$-$C_{16}$ alkyl dimethyl amine.

4. The process according to claim 1 wherein the oxidation is conducted using hydrogen peroxide or source of hydrogen peroxide.

5. The process according to claim 4 which is conducted at a pH in the range from about 6 to about 10.

6. The process according to claim 1 wherein said bicarbonate material is sodium bicarbonate.

7. The process according to claim 1 wherein said bicarbonate precursors are selected from the group consisting of alkali metal carbonates.

8. The process according to claim 1 which is carried out at a pH in the range of from about 7 to about 10.

9. The process according to claim 1, wherein:

a. the amine is a $C_{12}$-$C_{16}$ alkyl dimethylamine;

b. the oxidation is conducted using hydrogen peroxide;

c. the oxidation is conducted in the presence of sodium bicarbonate present at a level of from about 0.3% to about 2%, by weight of amine;

d. the oxidation is conducted at a pH in the range of from about 7 to about 10; and e. the oxidation is conducted over a temperature range of from about 45° C. to about 75° C.;

whereby said mono-long chain amine oxide has a nitrite content below about 3 ppm, a nitrosamine content below about 500 ppb, and active content of said surfactant of greater than about 30%, by weight of the composition, and wherein said process is essentially free of any phase-modifying solvent.

10. The process according to claim 1 wherein said bicarbonate material is present at a level of from about 0.3% to about 2.0%, by weight of amine.

11. The process according to claim 10 wherein said bicarbonate material is present at a level of from about 0.5% to about 1.5%, by weight of amine.

12. The process according to claim 1 wherein said mono-long chain amine oxide surfactant contains an active content of said surfactant of from about 31% to about 38%, by weight of the composition.

13. The process according to claim 12 wherein said active content of said surfactant is from about 32% to about 37%, by weight of the composition.

* * * * *